United States Patent
Van Kimmenade et al.

(10) Patent No.: US 8,048,412 B2
(45) Date of Patent: Nov. 1, 2011

(54) **ENZYME WITH MICROBIAL LYSIS ACTIVITY FROM *TRICHODERMA REESEI***

(75) Inventors: Anita Van Kimmenade, San Bruno, CA (US); Piet Van Solingen, Leiden (NL); Jian Yao, Sunnyvale, CA (US)

(73) Assignee: Danisco US Inc., Palo Alto, CA (US)

(*) Notice: Subject to any disclaimer, the term of this patent is extended or adjusted under 35 U.S.C. 154(b) by 92 days.

(21) Appl. No.: 12/369,135

(22) Filed: Feb. 11, 2009

(65) Prior Publication Data

US 2009/0232788 A1     Sep. 17, 2009

Related U.S. Application Data

(60) Provisional application No. 61/027,571, filed on Feb. 11, 2008.

(51) Int. Cl.
| | |
|---|---|
| *A61K 38/46* | (2006.01) |
| *A61K 8/00* | (2006.01) |
| *C12N 9/14* | (2006.01) |
| *C12P 21/06* | (2006.01) |
| *C07H 21/04* | (2006.01) |
| *D06M 16/00* | (2006.01) |
| *C11D 3/00* | (2006.01) |

(52) U.S. Cl. ......... 424/94.6; 424/61; 435/195; 435/263; 435/264; 435/69.1; 536/23.2; 8/137

(58) Field of Classification Search ................ 424/94.6, 424/61; 435/195, 263, 264, 69.1; 536/23.2; 8/137
See application file for complete search history.

(56) References Cited

U.S. PATENT DOCUMENTS

| | | | |
|---|---|---|---|
| 4,430,243 | A | 2/1984 | Bragg |
| 5,166,320 | A | 11/1992 | Wu et al. |
| 5,246,853 | A | 9/1993 | Clarkson et al. |
| 5,475,101 | A | 12/1995 | Ward et al. |
| 5,576,282 | A | 11/1996 | Miracle et al. |
| 5,595,967 | A | 1/1997 | Miracle et al. |
| 5,597,936 | A | 1/1997 | Perkins et al. |
| 5,650,322 | A | 7/1997 | Clarkson et al. |
| 5,874,276 | A | 2/1999 | Fowler et al. |
| 5,985,593 | A | 11/1999 | Thornton et al. |
| 6,022,725 | A | 2/2000 | Fowler et al. |
| 6,225,464 | B1 | 5/2001 | Hiler, II et al. |
| 6,268,328 | B1 | 7/2001 | Mitchinson et al. |
| 6,306,812 | B1 | 10/2001 | Perkins et al. |
| 6,326,348 | B1 | 12/2001 | Vinson et al. |

FOREIGN PATENT DOCUMENTS

| | | |
|---|---|---|
| EP | 0215594 | 9/1987 |
| EP | 0244234 | 11/1987 |
| WO | WO 92/06209 | 4/1992 |
| WO | WO 99/57157 | 11/1999 |
| WO | WO 00/32601 | 6/2000 |
| WO | WO 2005/001036 | 1/2005 |
| WO | WO 2005/011587 | 2/2005 |
| WO | WO 2005/080559 | 9/2005 |
| WO | WO 2006/060062 | 6/2006 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol.,2001, vol. 183 (8): 2405-2410.*
Sen et al., Developments in directed evolution for improving enzyme functions. Appl. Biochem. Biotechnol., 2007, vol. 143: 212-223.*
Wishart et al., A single mutation converts a novel phosphotyrosine binding domain into a dual-specificity phosphatase. J. Biol. Chem., 1995, vol. 270(45): 26782-26785.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Database UniProt [Online]Jul. 5, 2005 "SubName: Full=N,O-diacetly muramidase, putative; EC=<A HREF=http://srs.ebi.ac.uk/srsbin/cgi-bin/wgetz?[enzyme-ECNumber:3.2.1.*]+ -e>3.2.1.-</A>;" 56 pages printed Jul. 14, 2011.
Fleming (1922) Proc Royal Soc London B 93 pp. 306-317.
**Imoto et al., (1972) The Enzymes (Boyer, P.D., ed) $3^{rd}$ Ed, 7:665-668, Academic Press, Orlando, FL).
Zukaite et al., (2000) Lett Appl Microbiol 30:203-206.
**Molecular Closing: A Laboratory Manual, second edition (Sambrook et al, 1989).
**Oligonucleotide Synthesis (M. J. Gait, ed., 1984.
** Current Protocols in Molecular Biology (F.M. Ausubel et al., eds., 1994).
**PCR: The Polymerase Chain Reaction (Mullis et al., eds, 1994).
**Gene Transfer and Expession: A Laboratory Manual (Kriegler, 1990).
**Singleton, et al., Dictionary of Microbiology and Molecular Biology, second ed., John Wiley and Sons, New York (1994).
**Hale & Markham, The Harper Collins Dictionary of Biology, Harper Perennial, NY (1991).
**Alexopoulos, C.J. (1962) Introductory Mycology, Wiley, New York.
Altshul et al., J. Mol. Biol. 215 (1990) pp. 403-410.
Henikoff et al., Proc. Natl. Acad. Sci. 89 (1992) 10915-10919.
Karlin et al., Proc. Natl. Acad. Sci., 90 (1993) 5873-5877.
Higgins et al., Gene 73 (1988) 237-244.
Pearson et al., Proc. Natl. Acad. Sci. 85 *1988) 2444-2448.

(Continued)

*Primary Examiner* — Ganapathirama Raghu (57) ABSTRACT

The invention provides fungal polypeptides from *Trichoderma reesei* that possess anti-microbial activity, polynucleotides encoding the polypeptides, compositions comprising the polypeptides and polynucleotides, and methods of use, thereof.

3 Claims, 5 Drawing Sheets

OTHER PUBLICATIONS

Sheir-Neiss et al., Appl. Microbiol. Biotechnol. 20 (1984) 46-53.
Ward et al., Appl. Microbiol. Biotechnol. 39 (1993) 738-743.
Goedegebuur et al., Genet 41 (2002) 89-98.
Innis et al., Science 228 *1985) 21-26.
**Sambrook et al., (1989) Molecular Cloning: A Laboratory Manual, $2^{nd}$ Edition, Cold Spring Harbor Laboratory press.
Ferry et al., Proc. Natl. Acad. Sci., USA, 88 (1991) 8377-8381.
Kay et al., Human Gene Therapy, 3 (1992) 641-647.
Rosenfeld, Cell, 63 (1992) 143-155.
Herz and Gerard, Proc. Natl. Acad. Sci., USA, 90 (1993) 2812-2816.
Wu, J. Biol. Chem. 263 (1988) 14621-14624.
Wilson et al., J. Biol. Chem., 267 (1992) 963-967.
Acsadi et al., Nature 332 (1991) 815-818.
Wolff et al., Science 247 (1990) 1465-1468.
Cheng et al., Proc. Natl. Acad. Sci., USA, 90 (1993) 4455-4459.
Zelenin et al., FEBS Letts., 315 (1993) 29-32.
**R. Scopes (1982) Protein Purification, Springer-Verlag, N.Y.
**Deutscher (1990) Methods in Enzymology vol. 182; Guide to Protein Purification, Academic Press, Inc. N.Y.
**Bennet and Lasure (Eds.), More Gene Manipulations in Fungi, Academic Press, San Diego, pp. 396-428 Chapter 18, 1991.
**Finkelstein (1992) Biotechnology of Filamentous Fungi, Ch. 6, Finkelstein et al., eds., Butterworth-Heinemann, Boston, MA.
**Kinghorn et al., (1992) Applied Molecular Genetics of Filamentous Fungi, Blackie Academic and Professional, Chapman and Hall, London.
Kelley et al., EMBO J., 4 (1985) 475-479.
Penttila et al., Gene, 61 (1987) 155-164.
Campbell et al., Curr. Genet., 16 (1989) 53-56.
Harrki et al., Enzyme Microb. Technol., 13, (1991) 227-233.
Harrki et al., Bio Technol., 7 (1989) 596-603.
Nevalainen et al., "The Molecular Biology of Trichoderma and its Application to the Expression of Both Homologous and Heterologous Genes," Molecular Industrial Mycology, Leong and Berka, eds., Marcel Dekker Inc., NY, (1992) pp. 129-148.
Broun et al., "Catalytic Plasticity of Fatty Acid Modification Enzymes Underlying Chemical Diversity of Plant Lipids" Science 282 (1998) pp. 1315-1317.
Chica et al., "Semi-rational Approaches to Engineering Enzyme Activity: Combining the Benefits of Directed Evolution and Rational Design" Current Opinion in Biotechnology 16 (2005) pp. 378-384.
Devos et al., "Practical Limits of Function Prediction" PROTEINS: Structure, Function, and Genetics 41 (2000) pp. 98-107.
Seffernick et al., "Melamine Deaminase and Atrazine Chlorohydrolase: 98 Percent Identical But Functionally Different" J. Bacteriology 183:8 (2001) pp. 2405-2410.
Sen et al., "Developments in Directed Evolution for Improving Enzyme Functions" Appl. Biochem Biotechnology 143 (2007) pp. 212-223.
Wishart et al., "A Single Mutation Converts a Novel Phosphotyrosine Binding Domain into a Dual-specificity Phosphatase" J. Biological Chemistry, 270:45 (1995) pp. 26782-26785.
Whisstock et al., "Prediction of Protein Function from Protein Sequence and Structure" Quarterly Reviews of Biophysics 36, 3 (2003) pp. 307-340.
Witkowski et al,. "Conversion of a β-Ketoacyl Synthase to a Malonyl Decarboxylase by Replacement of the Active-Site Cysteine with Glutamine" Biochemistry 38 (1999) pp. 11643-11650.
PCT Search Report for PCT/US2009/033741 dated Jul. 10, 2009.

* cited by examiner

FIGURE 1

*T.reesei* destination vector pTrex3g-DEST

SDS-PAGE gel of TrLYS

Lane 1: NSP38
Lane 2: Host Strain
Lane 3: Mol. weight marker

FIGURE 4

Nucleotide sequence of the *T.reesei* lys1 gene (SEQ ID NO:3)

```
  1 atgaagtttc tgactcccct tgccgtccaa ttggcagccc ttgcctctat
 51 ggccagcgca accgtgccag gattcgacat ttcccactac caagccaccg
101 ttgactttgc caaagcctat gccgatggtg cacgctttgt gatcatcaag
151 gttcataccg tcttcccaac tctcatttca agatgaggtg ctaaactgct
201 gcttaggcta ctgagggcac cacctacact gacccagct tcagcgatca
251 ctataccaag gcgaccaatg ccggcttcat ccggggtggt taccactttg
301 cccagcccgc ctcctcttcc ggtgctgccc aagccaacta ctttctcaaa
351 cacggaggcg gctggtcagc ggacggcatc acacttcctg gtatgctgga
401 tcttgagtat gctcccagcg gcgacagctg ctatggcttg agcgcgagtg
451 ccatggtcag ctggatcaac gactttgtca cacttacca cgctgctacg
501 acccagtatc ctctcattta cacctccaca agctggtggc aactctgtac
551 tgggaacaat ggctcgtttg gtagcaaatc gcctcttgtt atcgcgcggt
601 atgctagctc tgttggggcg ctgcccaatg gctggagcgt ttatacaatc
651 tggcagaaca gtgatgcctc tccctggggt ggcgataatg atatcttcaa
701 cggaaatctc gcacaactgc agaagattgc ccgcggaagt tag
```

FIGURE 5

Deduced amino acid sequence of *T.reesei* lysozyme-A (SEQ ID NO:4)

```
  1  MKFLTPLAVQ  LAALASMASA  TVPGFDISHY  QATVDFAKAY  ADGARFVIIK
 51  ATEGTTYTDP  SFSDHYTKAT  NAGFIRGGYH  FAQPASSSGA  AQANYFLKHG
101  GGWSADGITL  PGMLDLEYAP  SGDSCYGLSA  SAMVSWINDF  VNTYHAATTQ
151  YPLIYTSTSW  WQLCTGNNGS  FGSKSPLVIA  RYASSVGALP  NGWSVYTIWQ
201  NSDASPWGGD  NDIFNGNLAQ  LQKIARGS
```

Bold text indicates the leader sequence

ENZYME WITH MICROBIAL LYSIS ACTIVITY FROM *TRICHODERMA REESEI*

PRIORITY

The present application claims priority to U.S. Provisional Patent Application Ser. No. 61/027,571, filed on Feb. 11, 2008, which is hereby incorporated by reference in its entirety.

FIELD OF THE INVENTION

The invention relates to a fungal polypeptide with anti-microbial activity, and methods of use, thereof.

BACKGROUND

Lysozyme (1,4-beta-N-acetylmuraminidase) is distributed in living tissue and is believed to play a role in defense against bacterial infections. (Fleming (1922) *Proc Royal Soc London* B39:306-317) Lysozyme functions by hydrolyzing polysaccharides in bacterial cell walls via a beta-glucosidase activity. The cell walls are thereby lysed, resulting in death of the cells. These enzymes act as bactericides, and this property explains their generalized presence in most of the biological fluids of mammals. For example, lysozyme is found, at various levels of concentration, in blood, tears, saliva, milk, etc., of mammals. It is also found in plants, e.g., in papaya. Lysozyme is present at high levels in hen egg white, from which it can be isolated relatively easily and with high purity. (Imoto et al. (1972) in *The Enzymes* (Boyer, P. D., ed) $3^{rd}$ Ed, 7:665-668, Academic Press, Orlando, Fla.)

Lysozyme is added to cheese, sausage and marine products for preservation purposes and is also used as a medicinal agent, for example, in hemostatic, anti-inflammation, or tissue regeneration applications. It can also be used to preserve milk components for pediatric use. (Japanese Patent No. 16780/70, 1970) In biotechnology applications, lysozyme may be added to a bacterial culture during recovery of expressed protein, facilitating release of protein from the cells. (Zukaite et al. (2000) *Lett Appl Microbiol* 30:203-206)

Lysozyme derived from hen egg white can induce an allergenic response in sensitive individuals, thus limiting its use in certain applications such as food preservation. There is a need for new enzymes with microbial lysis activity as an alternative to hen egg white lysozyme.

BRIEF SUMMARY

The present compositions and methods relate to a polypeptide from *Trichoderma reesei*, herein referred to as "NSP38," which has anti-microbial activity, polynucleotides encoding the NSP38 polypeptide, and methods of use, thereof.

In one aspect, the invention provides a polypeptide from *Trichoderma reesei* (termed "NSP38" herein) having anti-microbial activity. In some embodiments, the anti-microbial activity is a bacterial cell wall lysis activity, e.g., a 1,4-beta-N-acetylmuraminidase activity. In some embodiments, the anti-microbial activity is inhibition of growth (i.e., partial or complete inhibition) of a microbial cell, e.g., a bacterial or fungal cell, including an extended lag phase effect. In some embodiments, the polypeptide comprises, consists of, or consists essentially of the amino acid sequence set forth in SEQ ID NO:4, or a mature protein produced by cleavage of a signal sequence from SEQ ID NO:4. In some embodiments, the polypeptide comprises, consists of, or consists essentially of a variant of SEQ ID NO:4, or a variant of a mature protein produced by cleavage of a signal sequence from SEQ ID NO:4, having anti-microbial activity as described herein. The NSP38 polypeptide is catalytically active at acidic pH, e.g., pH lower than about 6.5, for example, about pH 6.

In another aspect, the invention provides a polynucleotide that encodes the NSP38 polypeptide or a variant thereof as described above. The polynucleotide may be in the form of an expression vector that comprises a polynucleotide encoding NSP38 or a variant thereof. The expression vector may be transformed into a host cell for expression of the NSP polypeptide or variant thereof.

In another aspect, the invention provides a method for expression of NSP38 polypeptide or a variant thereof, comprising culturing a host cell that has been transformed with a polynucleotide that encodes the polypeptide under conditions suitable for expression. In some embodiments, the method further comprises recovery of the polypeptide from the host cells and/or the culture medium.

In another aspect, the invention provides a method for inhibiting bacterial growth, comprising contacting a microbial cell (e.g., a bacterial or fungal cell) with an NSP38 polypeptide or variant thereof as described herein, wherein growth of the cell is inhibited. In some embodiments, the method comprises contacting a microbial culture with the polypeptide. In some embodiments, the method is conducted at acidic pH, e.g., pH lower than about 6.5, for example, about pH 6.

In another aspect, the invention provides a method for recovery of a microbially-produced protein, comprising contacting a microbial culture that is expressing the protein with an NSP38 polypeptide or variant thereof as described herein, thereby releasing the protein from the microbial cells.

In another aspect, the invention provides a composition for decreasing microbial load on fabric during cleaning, comprising NSP38 polypeptide or variant thereof in a cleaning composition. In some embodiments, the composition further comprises one or more of a lysin, protease, perhydrolase, lipase, phospholipase, oxidase, endoglycosidase, carohydrase, and other microbial cell wall degrading enzyme. In some embodiments, the composition produces less malodor than an identical composition that does not comprise the NSP38 polypeptide or variant thereof.

In another aspect, the invention provides a composition for use in food preservation.

Particular aspects and embodiments of the compositions and methods are set forth, below:

In one aspect, a recombinant polypeptide (NSP38) derived from *Trichoderma reesei* is provided, the polypeptide having anti-microbial activity. In some embodiments, the anti-microbial activity is bacterial cell wall lysis activity. In some embodiments, the anti-microbial activity is 1,4-beta-N-acetylmuraminidase activity. In some embodiments, the anti-microbial activity is characterized by partial or complete inhibition of growth of a microbial cell. In some embodiments, the anti-microbial activity is characterized by an extended lag phase effect in microbial growth. In particular embodiments, the microbial cell against which the polypeptide has anti-microbial activity is a bacterial or fungal cell. In some embodiments, the polypeptide has anti-microbial activity at acidic pH, e.g., less than pH 6.5 or less than pH 6.0.

In some embodiments, the polypeptide comprises an amino acid sequence having at least 85% sequence identity to the polypeptide set forth in SEQ ID NO:4, or a mature protein produced by cleavage of a signal sequence from said polypeptide. In some embodiments, the polypeptide consists essentially of an amino acid sequence having at least 85% sequence identity to the polypeptide set forth in SEQ ID NO:4, or a mature protein produced by cleavage of a signal sequence from said polypeptide. In some embodiments, the identity between the polypeptides and SEQ ID NO:4 is at least 85%, at least 86%, at least 87%, at least 88%, at least 89%, at least 90%, at least 91%, at least 92%, at least 93%, at least 94%, at least 95%, at least 96%, at least 97%, at least 98%, or even at least 99%. In particular embodiments, the polypeptide has the amino acid sequence as set forth in SEQ ID NO:4.

In another aspect, an isolated polynucleotide encoding the above polypeptide is provided. In a related aspect, a vector comprising such a polynucleotide is provided. In a related aspect, a host cell comprising such a vector is provided.

In another aspect, a composition for decreasing microbial load on fabric during cleaning, comprising a polypeptide as described, above, is provided. The composition may further comprise one or more of a lysin, a protease, a perhydrolase, a lipase, a phospholipase, an oxidase, an endoglycosidase, a carbohydrase, and another microbial cell wall degrading enzyme. The composition may produce less malodor than an identical composition that does not comprise the polypeptide or variant thereof. In another aspect, a composition for use in food preservation comprising a polypeptide as described, above, is provided. Related aspects include the use of a NSP38 polypeptide or a variant thereof in the preparation of composition as described.

In another aspect, a method for expressing an NSP38 polypeptide or a variant thereof, is provided, comprising culturing a host cell that has been transformed with a polynucleotide encoding the NSP38 polypeptide in culture medium under conditions suitable for expression. The method may further comprise recovering the polypeptide from the host cell or the culture medium. In some embodiments, the polypeptide (or variant thereof) comprises an amino acid sequence having at least 85% sequence identity to the polypeptide set forth in SEQ ID NO:4, or a mature protein produced by cleavage of a signal sequence from said polypeptide.

In another aspect, a method for inhibiting bacterial growth is provided, comprising contacting a microbial cell with an NSP38 polypeptide or variant thereof, thereby inhibiting the growth of the cell. In some embodiments, the method is conducted at acidic pH. In some embodiments, the polypeptide (or variant thereof) comprises an amino acid sequence having at least 85% sequence identity to the polypeptide set forth in SEQ ID NO:4, or a mature protein produced by cleavage of a signal sequence from said polypeptide.

In another aspect, a method for recovery of a microbially-produced protein is provided, comprising contacting microbial cells expressing the protein with an NSP38 polypeptide or variant thereof, thereby causing lysis of the cells and recovery the protein expressed by the microbial cells. In some embodiments, the polypeptide (or variant thereof) comprises an amino acid sequence having at least 85% sequence identity to the polypeptide set forth in SEQ ID NO:4, or a mature protein produced by cleavage of a signal sequence from said polypeptide.

These and other features of compositions and methods will be apparent from the description and drawings.

DETAILED DESCRIPTION

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, N.Y. (1991) provide a general dictionary of many of the terms used in this invention. Methods and materials similar or equivalent to those described herein can be used in the practice or testing of the present invention.

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

DEFINITIONS

As used herein, the term "polynucleotide" refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide," "nucleic acid," and "oligonucleotide" are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, the term "expression" refers to the process by which a polypeptide is produced based on the nucleic acid sequence of a gene. The process includes both transcription and translation.

As used herein, "expression vector" refers to a DNA construct containing a DNA coding sequence (e.g., gene sequence) that is operably linked to one or more suitable control sequence(s) capable of effecting expression of the coding sequence in a host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the invention is intended to include such other forms of expression vectors that serve equivalent functions and which are, or become, known in the art.

A "promoter" refers to a regulatory sequence that is involved in binding RNA polymerase to initiate transcription of a gene. A promoter may be an inducible promoter or a constitutive promoter. A non-limiting example of an inducible promoter which may be used in the invention is from the *Trichoderma reesei* cbh1 gene, which is an inducible promoter. An "inducible promoter" is a promoter that is active under environmental or developmental regulatory conditions.

The term "operably linked" refers to a juxtaposition or arrangement of specified elements that allows them to perform in concert to bring about an effect. For example, a promoter is operably linked to a coding sequence if it controls the transcription of the coding sequence.

"Under transcriptional control" is a term well understood in the art that indicates that transcription of a polynucleotide sequence depends on its being operably linked to an element which contributes to the initiation of, or promotes transcription.

"Under translational control" is a term well understood in the art that indicates a regulatory process which occurs after mRNA has been formed.

A "gene" refers to a DNA segment that is involved in producing a polypeptide and includes regions preceding and following the coding regions as well as intervening sequences (introns) between individual coding segments (exons).

As used herein, the term "host cell" refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a protein which facilitates the secretion of the mature form of the protein from the cell. The mature form of the extracellular protein lacks the signal sequence which is cleaved off during the secretion process.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "derived from" encompasses the terms "originated from," "obtained from," "obtainable from," "isolated from," and "created from," and generally indicates that one specified material find its origin in another specified material or has features that can be described with reference to the another specified material.

The term "filamentous fungi" refers to all filamentous forms of the subdivision Eumycotina (See, Alexopoulos, C. J. (1962), *Introductory Mycology*, Wiley, New York). These fungi are characterized by a vegetative mycelium with a cell wall composed of chitin, cellulose, and other complex polysaccharides, and are morphologically, physiologically, and genetically distinct from yeasts. Vegetative growth by filamentous fungi is by hyphal elongation and carbon catabolism is obligatorily aerobic. The filamentous fungal parent cell may be a cell of a species of *Trichoderma*, e.g., *Trichoderma reesei* (previously classified as *T. longibrachiatum* and currently also known as *Hypocrea jecorina*), *Trichoderma viride*, *Trichoderma koningii*, *Trichoderma harzianum*, and the like.

As used herein, the term "*Trichoderma*" or "*Trichoderma* sp.*"* refers to any fungal genus previously or currently classified as *Trichoderma*.

The term "culturing" refers to growing a population of microbial cells under suitable conditions for growth, in a liquid or solid medium.

The term "heterologous," with reference to a polynucleotide or protein, refers to a polynucleotide or protein that does not naturally occur in a specified host cell. It is intended that the term encompass proteins that are encoded by naturally occurring genes, mutated genes, and/or synthetic genes. In contrast, the term "homologous," with reference to a polynucleotide or protein, refers to a polynucleotide or protein that occurs naturally in the host cell.

The term "introduced," in the context of inserting a nucleic acid sequence into a cell, includes "transfection," "transformation," or "transduction" and refers to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed.

"Transfection" or "transformation" refers to the insertion of an exogenous polynucleotide into a host cell. The exogenous polynucleotide may be maintained as a non-integrated vector, for example, a plasmid, or alternatively, may be integrated into the host cell genome. The term "transfecting" or "transfection" is intended to encompass all conventional techniques for introducing nucleic acid into host cells. Examples of transfection techniques include, but are not limited to, calcium phosphate precipitation, DEAE-dextran-mediated transfection, lipofection, electroporation, and microinjection.

As used herein, the terms "transformed," "stably transformed," and "transgenic" refer to a cell that has a non-native (e.g., heterologous) nucleic acid sequence integrated into its genome or as an episomal plasmid that is maintained through multiple generations.

The terms "recovered," "isolated," "purified," and "separated" as used herein refer to a material (e.g., a protein, nucleic acid, or cell) that is removed from at least one component with which it is naturally associated. For example, these terms may refer to a material which is substantially or essentially free from components which normally accompany it as found in its native state, such as, for example, an intact biological system.

"Lysozyme" as used herein refers to an enzyme (i.e., a polypeptide having catalytic activity) that catalyzes hydrolysis of 1,4-beta linkages between N-acetylmuramic acid and N-acetyl-D-glucosamine residues in a peptidoglycan and between N-acetyl-D-glucosamine residues in chitodextrins. Lysozyme enzymes attack peptidoglycans (found in the cell walls of bacteria, particularly Gram-positive bacteria, by hydrolyzing the glycosidic bond that connects N-acetylmuramic acid with the forth carbon atom of N-acetylglucosamine.

A "signal sequence" (also termed "presequence," "signal peptide," "leader sequence," or "leader peptide") refers to a sequence of amino acids at the amino terminus of a nascent polypeptide that targets the polypeptide to the secretory pathway and is cleaved from the nascent polypeptide once it is translocated in the endoplasmic reticulum membrane.

Related (and derivative) proteins encompass "variant" proteins. Variant proteins differ from a parent protein and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence. The terms "homology" and "identity" are used without distinction.

As used herein, the term "analogous sequence" refers to a polypeptide sequence within a protein that provides a similar function, tertiary structure, and/or conserved residues with respect to a reference protein. For example, in epitope regions that contain an alpha helix or a beta sheet structure, replacement amino acid(s) in an analogous sequence maintain the same structural element. In some embodiments, analogous sequences are provided that result in a variant enzyme exhibiting a similar or improved function with respect to the parent protein from which the variant is derived.

As used herein, "homologous protein" refers to a protein (e.g., a perhydrolase enzyme) that has similar function (e.g., enzymatic activity) and/or structure as a reference protein (e.g., a lysozyme enzyme from a different source). Homologs may be from evolutionarily related or unrelated species. In some embodiments, a homolog has a quaternary, tertiary and/or primary structure similar to that of a reference protein, thereby potentially allowing for replacement of a segment or fragment in the reference protein with an analogous segment or fragment from the homolog, with reduced disruptiveness of structure and/or function of the reference protein in comparison with replacement of the segment or fragment with a sequence from a non-homologous protein.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins.

The phrases "substantially similar" and "substantially identical" in the context of at least two nucleic acids or polypeptides typically means that a polynucleotide or polypeptide comprises a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) *J. Mol. Biol.* 215:403-410; Henikoff et al. (1989) *Proc. Natl. Acad. Sci.* 89:10915; Karin et al. (1993) *Proc. Natl. Acad. Sci.* 90:5873; and Higgins et al. (1988) *Gene* 73:237). Software for performing BLAST analyses is publicly available through the National Center for Biotechnology Information. Also, databases may be searched using FASTA (Person et al. (1988) *Proc. Natl. Acad. Sci.* 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

The term "anti-microbial activity" refers to partial or complete inhibition of growth of a microbe (e.g., bacterial or fungal cell) and/or lysis of a microbial cell.

The abbreviation "MIC" refers to minimum inhibitory concentration.

"ATCC" refers to American Type Culture Collection located at Manassas, Va. 20108 (www.atcc.org).

"NRRL" refers to the Agricultural Research Service Culture Collection, National Center for Agricultural Utilization Research (and previously known as USDA Northern Regional Research Laboratory), Peoria, Ill.

"A," "an" and "the" include plural references unless the context clearly dictates otherwise.

NSP38 Polypeptides and Polynucleotides

Figure 4:
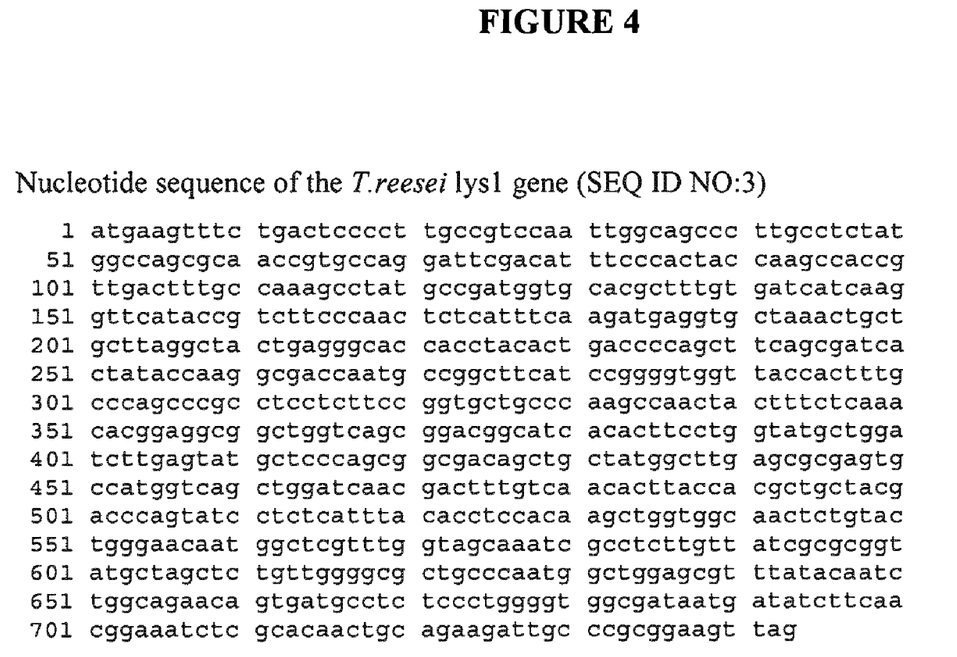
FIG. 4 depicts the nucleotide sequence for the NSP38 gene from *T. reesei* (SEQ ID NO:3).
Figure 5:
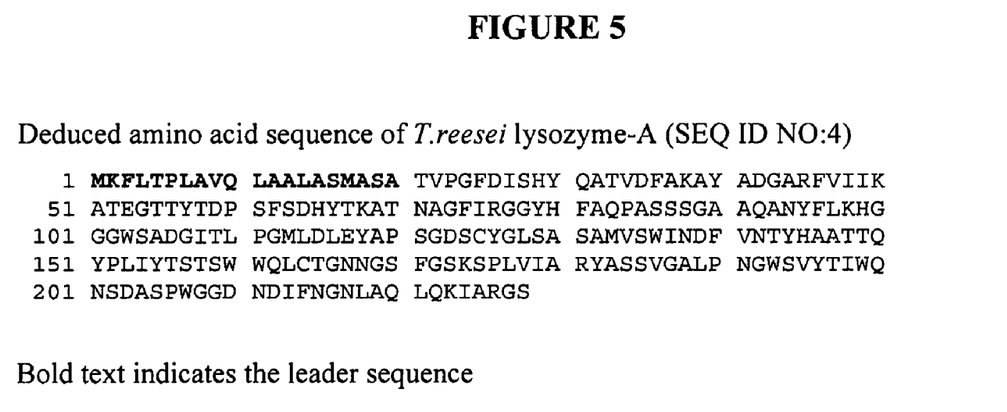
FIG. 5 depicts the deduced amino acid sequence of the NSP protein (SEQ ID NO:4).

One aspect of the invention provides a polypeptide from *Trichoderma reesei* herein referred to as "NSP38," which has anti-microbial activity. The *T. reesei* polynucleotide sequence that encodes this protein is shown in FIG. 4 (SEQ ID NO:3), and the deduced amino acid sequence is shown in FIG. 5 (SEQ ID NO:4). A signal sequence (shown in bold in FIG. 5) has been predicted using a software model relating this sequence to other known signal sequences. The deduced amino acid sequence includes 228 amino acid residues, including the predicted 20 amino acid signal sequence. The remaining sequence is that of the mature polypeptide.

Figure 1:
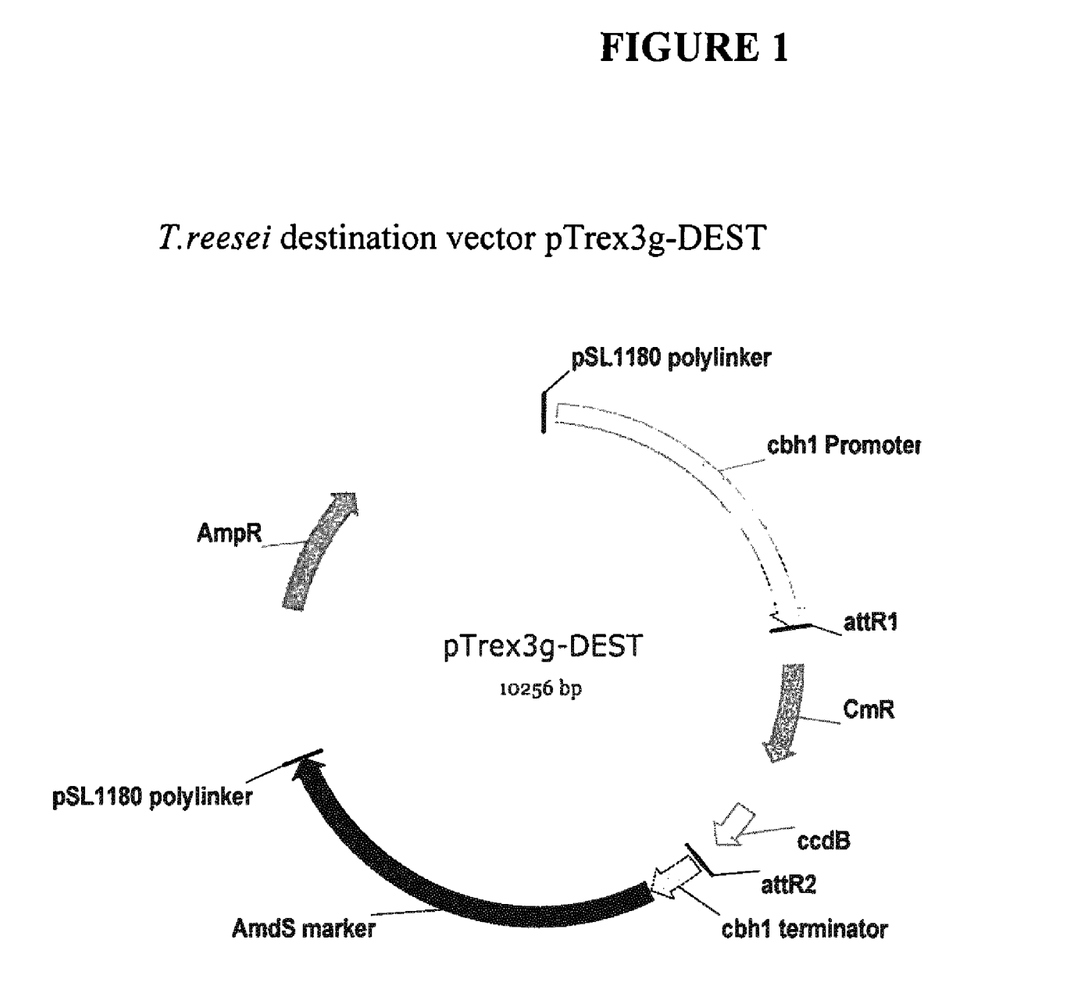
FIG. 1 is a schematic diagram of the pTrex3g-DEST *T. reesei* destination vector.
Figure 2:
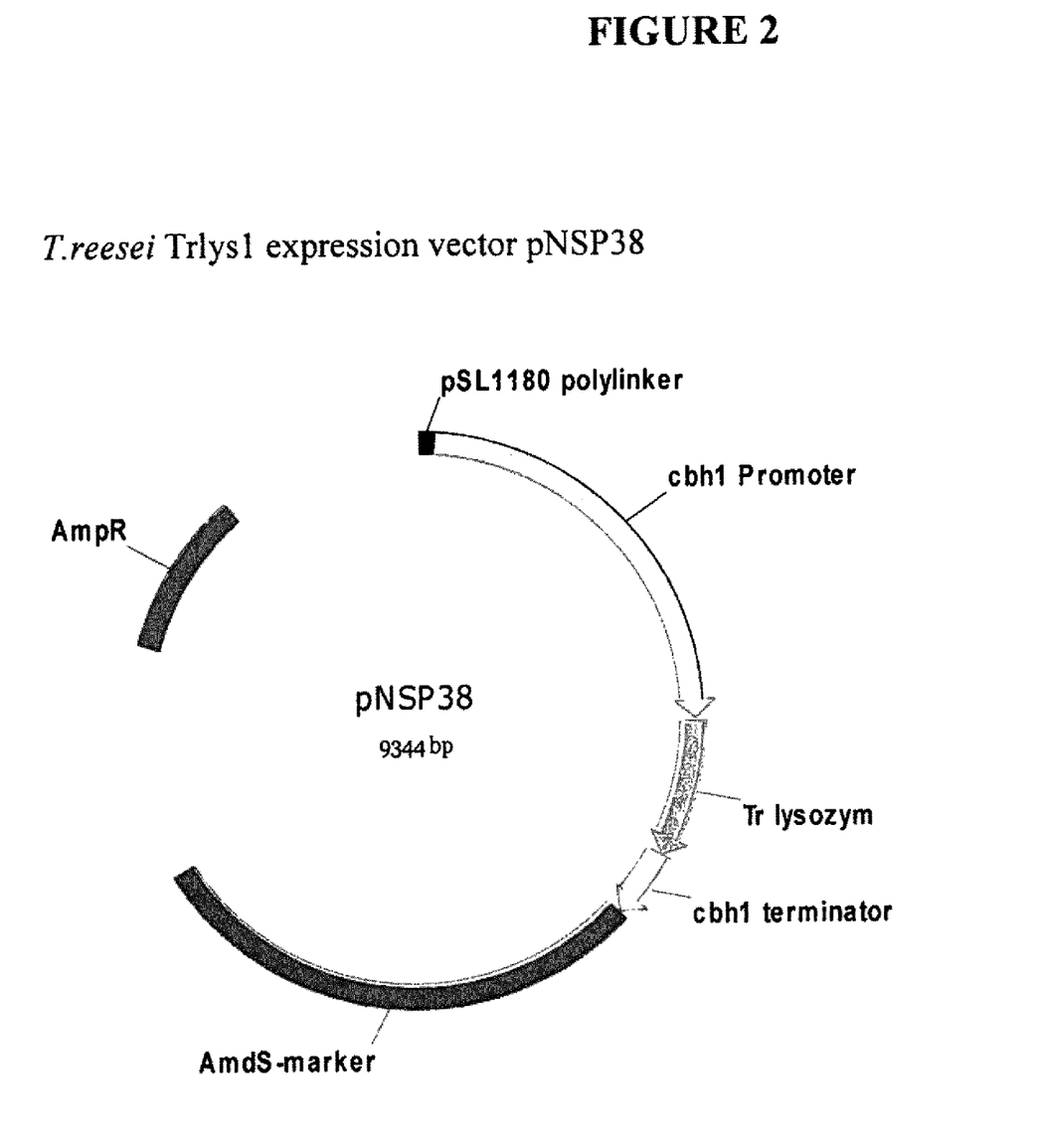
FIG. 2 is a schematic diagram of the Trlys1 expression vector for NSP38.
Figure 3:
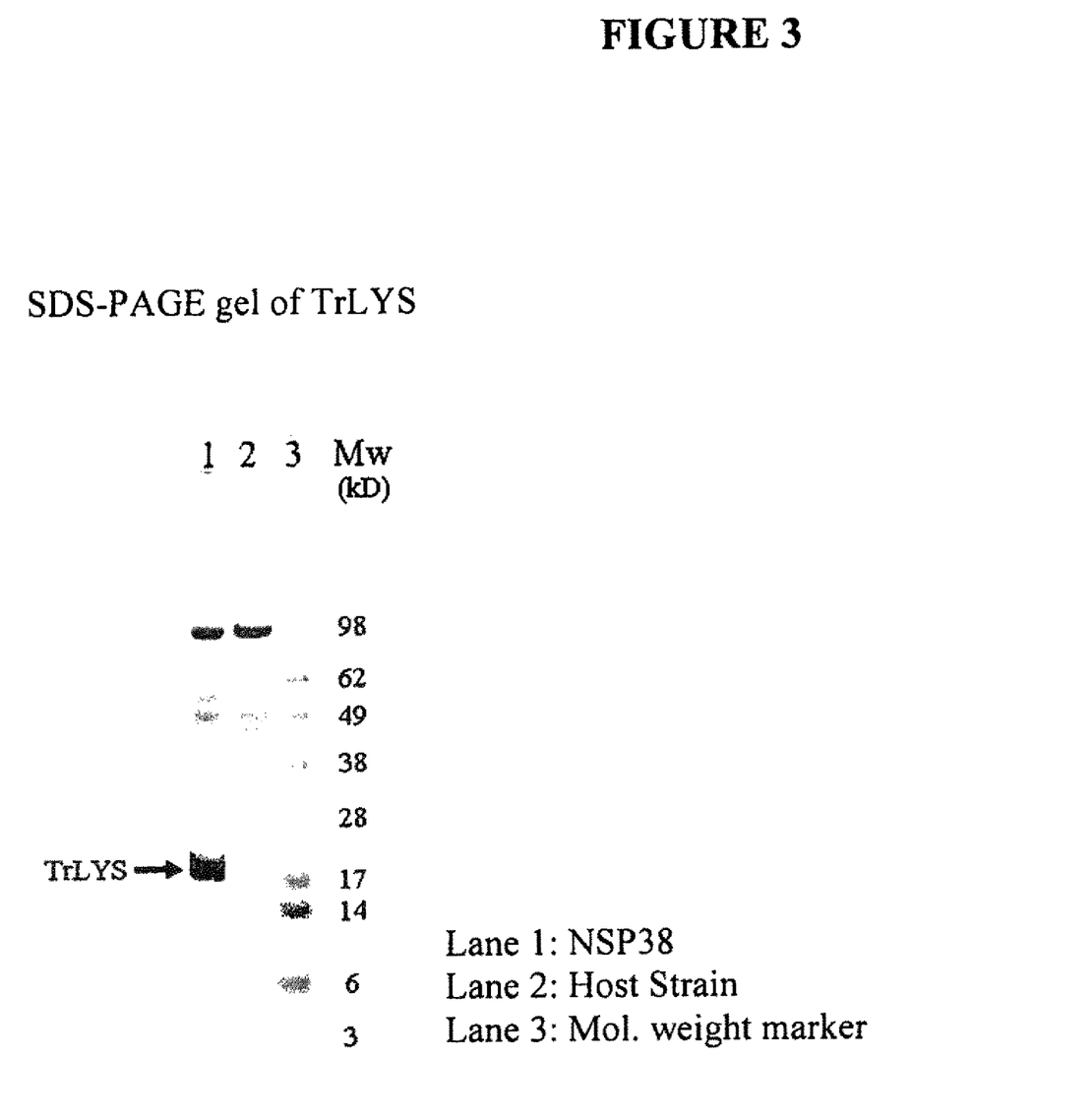
FIG. 3 is an SDS-PAGE gel of NSP38 expressed in *T. reesei*.

The polynucleotide sequence shown in FIG. 4 was transformed into *T. reesei* in the context of an expression vector as described in Example 1, below, and expressed as shown in FIG. 3. The molecular weight of the deduced mature polypeptide is 22,246 Daltons and the predicted isoelectric point based on amino acid composition is 5.60. As described in detail in the foregoing Examples, this polypeptide was shown to exhibit bacterial lysis activity with the highest activity being at acidic rather than neutral pH.

Another aspect of the invention provides a variants of SEQ ID NO:4 or a variant of a mature protein produced by cleavage of a signal sequence from SEQ ID NO:4, wherein the variant has the same or greater anti-microbial activity than the wild-type NSP38 polypeptide. Variants may include substitutions, deletions, insertions, or chemical modifications with respect to the polypeptide of SEQ ID NO:4. Exemplary substitutions for inclusion in variants are conservative amino acid substitutions, such as those listed in the following Table.

| Original Amino Acid Residue | Code | Acceptable Substitutions |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4- carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Yet another aspect of the invention provides a polynucleotide that encodes the NSP38 polypeptide or a variant thereof. Such a polynucleotide may be comprised within a vector, such as an expression vector, for production of the polypeptide in a microbial host cell. In one embodiment, an expression vector that comprises a polynucleotide that encodes the polypeptide of SEQ ID NO:4 is provided.

Host Cells

A further aspect of the invention provides host cells that can express an NSP polypeptide or variant thereof as described herein. i.e., comprising a polynucleotide encoding the NSP polypeptide or variant thereof. In some embodiments, the host cell is selected from bacterial, fungal, plant, and yeast cells. The term "host cell" includes the cells, progeny of the cells, and protoplasts created from the cells which are used to produce an NSP polypeptide or variant thereof.

In some embodiments, the host cells are fungal cells, e.g., filamentous fungal host cells. The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. A filamentous fungal host cell may be a cell of a species of, but not limited to, *Trichoderma*, (e.g., *Trichoderma reesei*, the asexual morph of *Hypocrea jecorina*, previously classified as *T. Iongibrachiatum*, *Trichoderma viride*, *Trichoderma koningii*, *Trichoderma harzianum*) (Sheir-Neirs et al., (1984) Appl. Microbiol. Biotechnol 20:46-53; ATCC No. 56765 and ATCC No. 26921); *Penicillium* sp., *Humicola* sp. (e.g., *H. insolens*, *H. lanuginosa* and *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, and *A. awamori*) (Ward et al., (1993) Appl. Microbiol. Biotechnol. 39:738-743 and Goedegebuur et al., (2002) Genet. 41:89-98), *Fusarium* sp., (e.g. *F. roseum, F. graminum F. cerealis, F. oxysporuim* and *F. venenatum*), *Neurospora* sp., (*N. crassa*), *Hypocrea* sp., *Mucor* sp., (*M. miehei*), *Rhizopus* sp. and *Emericella* sp. (See also, Innis et al., (1985) Science 228:21-26). The term "*Trichoderma*" or "*Trichoderma* sp." or "*Trichoderma* spp." refer to any fungal genus previously or currently classified as *Trichoderma*.

In some embodiments, the host cell is a *Trichoderma reesei* strain. Strains of *T. reesei* are known, with non-limiting examples including ATCC No. 13631, ATCC No. 26921, ATCC No. 56764, ATCC No. 56765, ATCC No. 56767, and NRRL No. 15709. In some embodiments, the host cell is derived from the RL-P37 *T. reesei* strain (described in Sheir-Neiss et al. (1984) *Appl. Microbiol. Biotechnology* 20:46-53. In one embodiment, the host cell is the Morph 1.1 (pyr+) *T. reesei* strain, a spontaneous pyr4 revertant of the quad-deleted RL-P37 *Trichoderma reesei* strain (described in PCT Application No. WO 05/001036).

In some embodiments, the host cell is a gram-positive bacterial cell. Non-limiting examples include strains of *Strep-*

*tomyces*, (e.g., *S. lividans, S. coelicolor* and *S. griseus*) and *Bacillus*. As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*."

In some embodiments the host cell is a gram-negative bacterial strain, such as *E. coli* or *Pseudomonas* sp. In other embodiments, the host cells may be yeast cells such as *Saccharomyces* sp., *Schizosaccharomyces* sp., *Pichia* sp., or *Candida* sp.

The host strain may have been previously manipulated through genetic engineering. In some embodiments, various native genes of the fungal host cell have been inactivated. Gene inactivation may be accomplished by complete or partial deletion, by insertional inactivation or by any other means which renders a gene nonfunctional for its intended purpose (such that the gene is prevented from expression of a functional protein). Where it is desired to obtain a fungal host cell having one or more inactivated genes known methods may be used (e.g. methods disclosed in U.S. Pat. Nos. 5,246,853 and 5,475,101 and WO 92/06209). The genes include, for example, genes encoding cellulolytic enzymes, such as endoglucanases (EG) and exocellobiohydrolases (CBH) (e.g., cbh1, cbh2, egl1, and egl3). U.S. Pat. No. 5,650,322 discloses derivative strains of RL-P37 having deletions in the cbh1 gene and the cbh2 gene. In some embodiments, when the host cell is a *Trichoderma* cell and particularly a *T. reesei* host cell, the cbh1, cbh2, egl1 and egl2 genes will be inactivated, e.g., by deletion. *Trichoderma reesei* host cells having quad-deleted proteins are set forth and described in U.S. Pat. No. 5,847,276 and WO 05/001036. In other embodiments, the host cell is a protease deficient or protease minus strain.

An expression vector encoding a polypeptide of the invention can be transfected or transformed into a host cell using standard techniques. Suitable methods for transfecting host cells can be found in Sambrook et al. (1989) *Molecular Cloning: A Laboratory Manual*, 2nd Edition, Cold Spring Harbor Laboratory press, and other laboratory textbooks. Nucleic acid can also be transferred into cells via a delivery mechanism suitable for introduction of nucleic acid into cells in vivo, such as via a retroviral vector (see e.g., Ferry et al. (1991) *Proc. Natl. Acad. Sci., USA*, 88: 8377-8381; and Kay et al. (1992) *Human Gene Therapy* 3: 641-647), an adenoviral vector (see, e.g., Rosenfeld (1992) *Cell* 68: 143-155; and Herz and Gerard (1993) *Proc. Natl. Acad. Sci., USA*, 90:2812-2816), receptor-mediated DNA uptake (see e.g., Wu, and Wu (1988) *J. Biol. Chem.* 263:14621; Wilson et al. (1992) *J. Biol. Chem.* 267: 963-967; and U.S. Pat. No. 5,166,320), direct injection of DNA (see, e.g., Acsadi et al. (1991) *Nature* 332: 815-818; and Wolff et al. (1990) *Science* 247:1465-1468) or particle bombardment (biolistics) (see e.g., Cheng et al. (1993) *Proc. Natl. Acad. Sci., USA*, 90:4455-4459; and Zelenin et al. (1993) *FEBS Letts*. 315: 29-32).

Certain vectors integrate into host cells at a low frequency. In order to identify these integrants, in some embodiments a gene that contains a selectable marker (e.g., drug resistance) is introduced into host cells along with the nucleic acid of interest. Examples of selectable markers include those which confer resistance to certain drugs, such as G418 and hygromycin. Selectable markers can be introduced on a separate vector from the nucleic acid of interest or on the same vector. Transfected host cells can then be identified by selecting for cells using the selectable marker. For example, if the selectable marker encodes a gene conferring neomycin resistance, host cells which have taken up nucleic acid can be identified by their growth in the presence of G418. Cells that have incorporated the selectable marker gene will survive, while the other cells die.

Once expressed, a polypeptide can be purified according to standard procedures of the art, including, but not limited to affinity purification, ammonium sulfate precipitation, ion exchange chromatography, or gel electrophoresis (see generally, R. Scopes (1982) *Protein Purification*, Springer-Verlag, N.Y.; Deutscher (1990) *Methods in Enzymology* Vol. 182: *Guide to Protein Purification, Academic Press*, Inc. N.Y.).

Vectors

In accordance with the invention, a vector comprising a polynucleotide sequence that encodes NSP38 or a variant thereof is introduced into a *Trichoderma* host cell. Typically, a polypeptide comprising NSP38 or a variant thereof is expressed from an expression vector comprising a polynucleotide encoding the polypeptide and comprising regulatory sequence(s) operably linked to the coding sequence.

The vector may be any vector that can be introduced into and replicated in a host cell, e.g., a *Trichoderma* cell. Examples of suitable vectors may be found, for example, in Sambrook et al. (1989), supra, Ausubel (1994), supra, van den Hondel et al. (1991) in Bennet and Lasure (Eds.), *More Gene Manipulations in Fungi*, Academic Press, San Diego, pp. 396-428, and U.S. Pat. No. 5,874,276. Examples of useful vectors include, but are not limited to, pFB6, pBR322, PUC18, pUC100, and pENTR/D.

Typically, a polynucleotide encoding NSP38 or a variant thereof is operably linked to a suitable promoter that exhibits transcriptional activity in the *Trichoderma* host cell. The promoter may be derived from a gene encoding a protein that is either homologous or heterologous to the host cell. Suitable nonlimiting examples of promoters include cbh1, cbh2, egl1, and egl2. In some embodiments, the promoter is native to the host cell. For example, when *T. reesei* is the host cell, the promoter may be a native *T. reesei* promoter. In one embodiment, the promoter is *T. reesei* cbh1, which is an inducible promoter and has been deposited in GenBank under Accession No. D86235. In another embodiment, the promoter is heterologous to the host cell.

In some embodiments, the coding sequence is operably linked to a polynucleotide sequence encoding a signal sequence. In some embodiments, the signal sequence is one that is naturally associated with the gene to be expressed. In some embodiments, the signal sequence is the *T. reesei* cbh1 signal sequence. In some embodiments, a vector to be introduced into a *Trichoderma* host cell comprises a signal sequence and a promoter sequence derived from the same source. In some embodiments, the signal sequence and the promoter sequence are derived from different sources.

In some embodiments, the vector also includes a termination sequence. In some embodiments, a vector to be introduced into a *Trichoderma* host cell comprises a termination sequence and a promoter sequence derived from the same source. In some embodiments, the termination sequence and the promoter sequence are derived from different sources. One nonlimiting example of a suitable terminator sequence is the terminator sequence of cbh1 derived from a *Trichoderma* strain, such as a strain of *Trichoderma reesei*.

In some embodiments, the vector includes a selectable marker. Examples of suitable selectable markers include, but are not limited to, genes that confer resistance to an antimicrobial compound, e.g., hygromycin, phleomycin. Nutritional selectable markers may also be used, e.g., amdS, argB, pyr4. Markers useful in vector systems for transformation of *Trichoderma* are known in the art. (See, e.g., Finkelstein (1992) *Biotechnology of Filamentous Fungi*, Ch. 6, Finkelstein et al., eds., Butterworth-Heinemann, Boston, Mass.; Kinghorn et al. (1992) *Applied Molecular Genetics of Filamentous Fungi*, Blackie Academic and Professional, Chapman and Hall, London). In one embodiment, the selectable marker is the amdS gene, which encodes the enzyme acetamidase, allowing transformed cells to grow on acetamide as a nitrogen source. The use of *A. nidulans* amdS gene as a selectable marker is described in Kelley et al. (1985) *EMBO J.* 4:475-497 and Penttila et al. (1987) *Gene* 61:155-164.

An expression vector comprising a polynucleotide sequence encoding NSP38 or a variant thereof may be any vector that is capable of replicating autonomously in a *Trichoderma* host cell or integrating into the DNA of the host cell. In some embodiments, the expression vector is a plasmid.

Methods of making a DNA construct comprising a polynucleotide encoding a polypeptide and other sequences such as a promoter and a terminator, and to insert them into a suitable vector are well known in the art. Linking of polynucleotide sequences is generally accomplished by ligation at convenient restriction sites. If such sites do not exist, synthetic oligonucleotide linkers are used in accordance with conventional practices. (See, e.g., Sambrook (1989), supra; Bennett and Lasure (1991), supra, pp. 70-76.)

Introduction of Vectors into Host Cells

Introduction of a vector comprising a polynucleotide sequence that encodes a polypeptide into a host cell may be performed using any of a number of well known techniques in the art, for example, transformation, electroporation, nuclear microinjection, transduction, transfection (e.g., lipofection or DEAE-Dextrin mediated transfection), incubation with calcium phosphate DNA precipitate, high velocity bombardment with DNA-coated microprojectiles, or protoplast fusion.

In some embodiments, stable transformants are produced, whereby the polynucleotide encoding the polypeptide is stably integrated into the host cell chromosome. Transformants are then purified by known techniques.

In one embodiment, stable transformants including an amdS marker are distinguishable from unstable transformants by their faster growth rate and the formation of circular colonies with a smooth, rather than ragged, outline on solid culture medium that contains acetamide. Additionally, in some cases a further test of stability is conducted by growing the transformants on solid non-selective medium (i.e., medium that lacks acetamide), harvesting spores from this culture medium, and determining the percentage of these spores that subsequently germinate and grow on selective medium that contains acetamide. Alternatively, other methods known in the art may be used to select transformants.

In one embodiment, preparation of *Trichoderma* host cells for transformation involves the preparation of protoplasts from fungal mycelia. (See, e.g., Campbell et al. (1989) *Curr. Genet.* 16:53-56.) In some embodiments, the mycelia are obtained from germinated vegetative spores. The mycelia are treated with an enzyme that digests the cell wall, resulting in protoplasts. The protoplasts are protected by the presence of an osmotic stabilizer in the suspension medium. Such stabilizers include, for example, sorbitol, mannitol, potassium chloride, and magnesium sulfate. Typically, stabilizer concentration is in the range of about 0.8 M to about 1.2 M. In one embodiment, sorbitol is present in the suspension medium at a concentration of about 1.2 M.

Typically, uptake of DNA into a host *Trichoderma* cell is dependent upon calcium ion concentration in the uptake solution. Generally, about 10 mM to about 50 mM $CaCl_2$ is included in the uptake solution. In addition, the uptake solution also typically includes a buffering system (e.g., TE buffer (10 mM Tris, pH 7.4; 1 mM EDTA) or 10 mM morpholinepropanesulfonic acid (MOPS), pH 6.0) and polyethylene glycol (PEG). Although not wishing to be bound by theory, PEG may act to fuse the cell membranes, thus permitting the contents of the medium to be delivered into the cytoplasm of a *Trichoderma* cell and transfer of plasmid DNA to the nucleus. This fusion typically results in integration of multiple copies of plasmid DNA into the host chromosome.

Often, a suspension containing *Trichoderma* protoplasts or cells that have been subjected to a permeability treatment at a density of about $10^5$ to about $10^7$ per ml, typically about $2 \times 10^6$ per ml, is used for transformation. A volume of 100 t of these protoplasts or cells in an appropriate solution (e.g., a solution containing 1.2 M sorbitol 50 mM $CaCl_2$) is mixed with DNA. Generally, a high concentration of PEG is added to the uptake solution. For example, about 0.1 to about 1 volume of 25% PEG 4000 can be added to the protoplast suspension. In one embodiment, about 0.25 volume of 25% PEG 4000 is added. Additives including but not limited to dimethyl sulfoxide, heparin, spermidine, and potassium chloride may be added to the uptake solution and aid in transformation. Typically, the uptake mixture is then incubated at 0° C. for about 10 to about 30 minutes. Additional PEG may then be added to the mixture to further enhance the uptake of the desired gene or polynucleotide sequence. For example, about 5 to about 15 volumes 25% PEG 4000 may be added. However, greater or lesser volumes may be suitable. The amount of added 25% PEG 4000 is often about 10 times the volume of the transformation mixture. After addition of PEG, the transformation mixture may then be incubated either at room temperature or on ice, followed by addition of a sorbitol and calcium chloride solution. The protoplast suspension is then added to aliquots of a growth medium, e.g., molten growth medium, which only permits growth of transformants.

Production of NSP38 Polypeptide

Expression of protein in *Trichoderma* is described, for example, in U.S. Pat. Nos. 6,022,725 and 6,268,328, Harkki et al. (1991) *Enzyme Microb. Technol.* 13:227-233, Harrki et al. (1989) *Bio Technol.* 7:596-603, EP 244,234, EP 215,594, and Nevalainen et al. (1992) "The Molecular Biology of *Trichoderma* and its Application to the Expression of Both Homologous and Heterologous Genes," in *Molecular Industrial Mycology*, Leong and Berka, eds., Marcel Dekker Inc., NY, pp. 129-148.

Generally, *Trichoderma* host cells are cultured in a standard medium containing physiological salts and nutrients. Common commercially prepared media (e.g., yeast malt extract (YM) broth; Luria Bertani (LB) broth; Sabouraud Dextrose (SD) broth) may be used. Typically, cells are cultured at approximately 28° C. in shake cultures or fermenters until desired levels of expression are achieved. In some embodiments in which the *T. reesei* cbh1 promoter is used, lactose or a glucose-sophorose mixture is included as the carbon source in the media.

Methods

In one aspect, the invention provides a method for expression of NSP38 polypeptide or a variant thereof as described herein. In one embodiment, the method comprises transforming a host cell, e.g., a *Trichoderma* host cell, with an expression vector comprising a polynucleotide that encodes NSP38 polypeptide or a variant thereof, and culturing the host cell under conditions suitable for expression of the polypeptide. In one embodiment, the method comprises culturing a host cell, e.g., a *Trichoderma* host cell, that has been transformed with an expression vector comprising a polynucleotide that encodes NSP38 polypeptide or a variant thereof, under conditions suitable for expression of the polypeptide. In some embodiment, the polynucleotide comprises, consists of, or consists essentially of the sequence set forth in SEQ ID NO:3. In some embodiments, the method further comprises recovery of the NSP38 polypeptide from the culture medium.

In another aspect, the invention provides a method for inhibiting bacterial growth, comprising contacting a microbial cell with an NSP38 polypeptide or variant thereof as described herein, wherein growth of the cell is inhibited. In one embodiment, the microbial cell is a bacterial cell. In one embodiment, the microbial cell is a fungal cell. In some embodiments, the method is conducted at acidic pH, for example, pH of any of about 6.5, 6, 5.5, or 5.

In another aspect, the invention provides a method for recovery of a microbially-produced protein, comprising contacting a microbial culture that is expressing a protein of interest with an NSP38 polypeptide or a variant thereof as described herein, thereby degrading microbial cell walls and releasing the protein of interest from the microbial cells.

In another aspect, provides a method for decreasing the microbial load on fabric in a cleaning application, such as a household laundry application, comprising cleaning the fabric with a detergent composition that comprises NSP38 polypeptide or a variant thereof as described herein, wherein the microbial load is less than when an identical detergent composition is used that does not comprise the NSP38 polypeptide or variant thereof. In some embodiments, malodor is decreased relative to a detergent composition that does not comprise the NSP38 polypeptide or variant thereof.

In another aspect, the invention provides a method for food preservation, comprising contacting a food product with NSP38 polypeptide or a variant thereof to reduce or eliminate microbial growth in the food product. Nonlimiting examples of food products in which such a method for food preservation may be used include dairy products, meat products, and fish or seafood products.

Compositions

In a further aspect, invention provides compositions comprising an NSP38 polypeptide or variant thereof as described herein.

Cleaning Compositions

A composition for decreasing microbial load on fabric during cleaning is provided. The composition comprises NSP38 polypeptide or a variant thereof in a cleaning composition, e.g., a detergent composition. In some embodiments, the composition further comprises one or more enzymes that are beneficial in a cleaning composition, including, but not limited to, a lysine, a protease, a perhydrolase, a lipase, a phospholipase, an oxidase, an endoglycosidase, a carbohydrase, and/or another microbial cell wall degrading enzyme. In some embodiments, the composition produces less malodor than an identical composition that does not comprise the NSP38 polypeptide or variant thereof.

Adjunct materials may also be included in the cleaning composition, for example, to assist or enhance cleaning performance, for treatment of the substrate to be cleaned, or to modify the aesthetics of the cleaning composition as is the case with perfumes, colorants, dyes or the like. It is understood that such adjuncts are in addition to the enzyme-containing granules as described herein. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are described in U.S. Pat. Nos. 5,576,282, 6,306,812, and 6,326,348.

Surfactants—A cleaning composition as described herein may comprise a surfactant or surfactant system wherein the surfactant can be selected from nonionic surfactants, anionic surfactants, cationic surfactants, ampholytic surfactants, zwitterionic surfactants, semi-polar nonionic surfactants, and mixtures thereof. A surfactant is typically present at a level of about 0.1% to about 60%, about 1% to about 50% or about 5% to about 40% by weight of the subject cleaning composition.

Builders—A cleaning composition as described herein may comprise one or more detergent builder or builder system. When a builder is used, the subject cleaning composition will typically comprise at least about 1%, about 3% to about 60%, or about 5% to about 40% builder by weight of the subject cleaning composition.

Builders include, but are not limited to, the alkali metal, ammonium and alkanolammonium salts of polyphosphates, alkali metal silicates, alkaline earth and alkali metal C carbonates, aluminosilicate builders, polycarboxylate compounds ether hydroxypolycarboxylates, copolymers of maleic anhydride with ethylene or vinyl methyl ether, 1, 3, 5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—A cleaning composition as described herein may contain one or more chelating agent. Suitable chelating agents include, but are not limited to, copper, iron and/or manganese chelating agents and mixtures thereof. When a chelating agent is used, the cleaning composition may comprise about 0.1% to about 15%, or about 3.0% to about 10% chelating agent by weight of the subject cleaning composition.

Deposition Aid—A cleaning composition as described herein may contain a one or more deposition aid. Suitable deposition aids include, but are not limited to, polyethylene glycol, polypropylene glycol, polycarboxylate, soil release polymers such as polytelephthalic acid, and clays such as Kaolinite, montmorillonite, atapulgite, illite, bentonite, halloysite, and mixtures thereof.

Dye Transfer Inhibiting Agents—A cleaning composition as described herein may include one or more dye transfer inhibiting agent. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, and polyvinylimidazoles, and mixtures thereof. When present in a subject cleaning composition, dye transfer inhibiting agent may be present at levels of about 0.0001% to about 10%, about 0.01% to about 5%, or about 0.1% to about 3% by weight of the cleaning composition.

Dispersants—A cleaning composition as described herein may contain one or more dispersant. Suitable water-soluble organic dispersants include, but are not limited to, the homo- or co-polymeric acids or their salts, in which the polycarboxylic acid comprises at least two carboxyl radicals separated from each other by not more than two carbon atoms.

Enzyme Stabilizers—Enzymes for use in detergents can be stabilized by various techniques. Enzymes employed herein can be stabilized, for example, by the presence of water-soluble sources of calcium and/or magnesium ions in the finished compositions that provide such ions to the enzymes.

Catalytic Metal Complexes—A cleaning composition as described herein may include one or more catalytic metal complex. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243. Manganese-containing catalysts useful herein are known, and are described, for example, in U.S. Pat. No. 5,576,282. Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. No. 5,597,936 and U.S. Pat. No. 5,595,967.

Compositions herein may also include a transition metal complex of a macropolycyclic rigid ligand—abbreviated as "MRL". As a practical matter, and not by way of limitation, the compositions and cleaning processes herein can be adjusted to provide on the order of at least one part per hundred million of the active MRL species in the aqueous washing medium, and will often provide about 0.005 ppm to about 25 ppm, about 0.05 ppm to about 10 ppm, or about 0.1 ppm to about 5 ppm, of the MRL in the wash liquor. Suitable transition-metals in a transition-metal bleach catalyst include manganese, iron and chromium. In one embodiment, an MRL is an ultra-rigid ligand that is cross-bridged, such as 5,12-diethyl-1,5,8,12-tetraazabicyclo[6.6.2] hexadecane. Suitable transition metal MRLs are readily prepared by known procedures, such as taught for example in PCT Application No. WO 00/332601 and U.S. Pat. No. 6,225,464.

The cleaning compositions disclosed herein of can be used to clean a situs on a surface or fabric. Typically at least a portion of the situs is contacted with a cleaning composition as described above, in neat form or diluted in a wash liquor, and then the situs is optionally washed and/or rinsed. Washing includes, but is not limited to, scrubbing, and mechanical agitation. A fabric may comprise most any fabric capable of being laundered in normal consumer use conditions. The disclosed cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

Food Preservation Compositions

A composition for food preservation is provided. The composition comprises NSP38 polypeptide or a variant thereof, and is useful for reducing or eliminating bacterial growth in a food product. Non-limiting examples of food preservation compositions that may include NSP38 polypeptide or a variant thereof include a lacto-anti-microbial composition (e.g., lactoferrin, lactoglobulins, lactolipids), an ovo-antimicrobial composition (e.g., ovotransferrin, avidin), a phyto-antimicrobial composition (e.g., phyto-phenols, saponins, catechins), a bacto-antimicrobial composition (e.g., bacteriocins, reuterin), an acid-antimicrobial composition (e.g., lactic acid, sorbic acid, citric acid), a milieu-antimicrobial composition (e.g., polyphosphates), a composition comprising enzymes with antimicrobial effects, and a composition comprising medium-chain fatty acids and esters.

The following examples are intended to illustrate, but not limit, the invention.

EXAMPLES

Example 1

Cloning and Expression of NSP38 in *Trichoderma reesei*

A. Construction of Expression Vectors Comprising a Polynucleotide Encoding *Trichoderma reesei* Lysozyme A.

Genomic DNA was extracted from *T. reesei* strain QM6a. PCR primers were designed based on the putative protease sequence found in Trire2/scaffold_2:146675-147417 of the *T. reesei* genome (JGI *T. reesei* genome v2.0). The forward primer contained a motif for directional cloning into the PDONR™ 201 (Invitrogen, Carlsbad, Calif. USA).

The sequence of the NSP381 forward primer was ATGAAGTTTCTGACTCCCCTTGCC (SEQ ID NO: 1), and the sequence of the NSP382 reverse primer was CTAACTTCCGCGGGCAATCTTCTG (SEQ ID NO:2).

The 0.8 kb PCR product was purified by gel extraction (Gel Purification kit, Qiagen) and cloned into PDONR™ 201, according to the Invitrogen Gateway system protocol.

The expression cassette comprising the DNA sequence (SEQ ID NO:3) was cloned into PDONR™ 201, a GATEWAY® Entry vector (Invitrogen, Carlsbad, Calif.). The Trlys1 expression cassette was cloned into the Gateway compatible destination vector pTrex3g-DEST (FIG. 1), which is also described in PCT Application No. WO 06/060062, by the GATEWAY® LR recombination reaction. The pTrex3g-Trlys1 expression vector (FIG. 2) enabled the expression of the TrLYS protein (SEQ ID NO:4) in a *Trichoderma reesei* host.

B. Transformation.

The pTrex3g-Trlys1 expression vector was transformed into a *T. reesei* host strain derived from RL-P37 (IA52) and having various gene deletions (Δcbh1, Δcbh2, Δegl1, Δegl2) using particle bombardment by the PDS-1000/Helium System (BioRad Cat. No. 165-02257). The protocol is outlined below, and reference is also made to examples 6 and 11 of PCT Application No. WO 05/001036.

A suspension of spores (approximately $5\times10^8$ spores/ml) from the strain of *T. reesei* was prepared. 100 μl-200 μl of spore suspension was spread onto the center of plates of Minimal Medium (MM) acetamide medium. (MM acetamide medium had the following composition: 0.6 g/L acetamide; 1.68 g/L CsC1; 20 g/L glucose; 20 g/L $KH_2PO_4$; 0.6 g/L $CaCl_2.2H_2O$; 1 ml/L 1000× trace elements solution; 20 g/L Noble agar; pH 5.5.) 1000× trace elements solution contained 5.0 g/L $FeSO_4.7H_2O$; 1.6 g/L $MnSO_4$; 1.4 g/L $ZnSO_4.7H_2O$ and 1.0 g/L $CoCl_2.6H_2O$. The spore suspension was allowed to dry on the surface of the MM acetamide medium.

Transformation was performed in accordance with the manufacturer's instructions. Briefly, 60 mg of M10 tungsten particles were placed in a microcentrifuge tube. 1 mL of ethanol was added and allowed to stand for 15 minutes. The particles were centrifuged at 15,000 rpm for 15 seconds. The ethanol was removed and the particles were washed three times with sterile $dH_2O$, then 1 mL of 50% (v/v) sterile glycerol was added. 25 µl of tungsten particle suspension was placed into a microcentrifuge tube. While continuously mixing, the following were added: 0.5-5 µl (100-200 ng/µl) of plasmid DNA, 25 µl of 2.5M $CaCl_2$ and 10 µl of 0.1M spermidine. The particles were centrifuged for 3 seconds. The supernatant was removed and the particles were washed with 200 µl of 70% (v/v) ethanol and centrifuged for 3 seconds. The supernatant was removed and 24 µl 100% ethanol was added, mixed by pipetting, and the tube was placed in an ultrasonic bath. 8 µl aliquots of particles were removed and placed onto the center of macrocarrier disks that were held in a desiccator. Once the tungsten/DNA solution had dried, the microcarrier disk was placed in the bombardment chamber along with the plate of MM acetamide with spores and the bombardment process was performed according to the manufacturer's instructions. After bombardment of the plated spores with the tungsten/DNA particles, the plates were incubated at 28° C. Transformed colonies were picked to fresh plates of MM acetamide after 4 days (Pentillä et al. (1987) *Gene* 61: 155-164).

C. Demonstration of the Production of the Expressed Trlys1 in Transformed Cells.

After 5 days growth on MM acetamide plates, transformants displaying stable morphology were inoculated into 250 ml shake flasks containing 30 ml of Proflo medium. (Proflo medium contained: 30 g/L α-lactose; 6.5 g/L $(NH_4)_2SO_4$; 2 g/L $KH_2PO_4$; 0.3 g/L $MgSO_4.7H_2O$; 0.2 g/L $CaCl_2$; 1 ml/L 1000× trace element salt solution; 2 ml/L 10% Tween 80; 22.5 g/L ProFlo cottonseed flour (Traders protein, Memphis, Tenn.); 0.72 g/L $CaCO_3$.) After two days growth at 28° C. and 140 rpm, 10% of the Proflo culture was transferred to a 250 ml shake flask containing 30 ml of Lactose Defined Media. The composition of the Lactose defined Media was as follows: 5 g/L $(NH_4)_2SO_4$; 33 g/L PIPPS buffers; 9 g/L casamino acids; 4.5 g/L $KH_2PO_4$; 1.0 g/L $MgSO_4$ $7H_2O$; 5 ml/L Mazu DF60-P antifoam (Mazur Chemicals, Ill.); 1000× trace element solution; pH 5.5. 40 ml/L of 40% (w/v) lactose solution was added to the medium after sterilization. The Lactose Defined medium shake flasks were at 28° C., 140 rpm for 4-5 days.

Mycelia were removed by centrifugation and the supernatant was analyzed for total protein (BCA Protein Assay Kit, Pierce Cat. No. 23225). Samples of the culture supernatant were mixed with an appropriate volume of 2× sample loading buffer with reducing agent. The protein profile was determined by SDS-PAGE electrophoresis on NUPAGE® Novex 10% Bis-Tris Gel with MES SDS Running Buffer (Invitrogen, Carlsbad, Calif., USA) (FIG. 3).

Example 2

Bacterial Lysis Activity of NSP38

1.25 ml of an overnight culture of *Bacillus licheniformis* grown in LB medium (Luria-Bertani medium: 10 g/l tryptone, 5 g/l yeast extract, 10 g/l NaCl, pH adjusted to 7.0 with NaOH) for 16 hours at 37° C. was centrifuged, and cells were resuspended in either 400 µl TEN buffer (20 mM Tris/1 mM EDTA/50 mM NaCl), pH 7.5, or P1 buffer from the Qiagen plasmid prep kit. 1 µl of NSP38 ultrafiltration concentrate (UFC) was added and incubated at 37° C. NSP38 UFC was concentrated culture supernatant from a *T. reesei* fermentation as described in Example 1, and contained 127 mg/ml total protein (estimated at approximately 100 mg/ml NSP38 protein).

A positive control contained 2 µl READY-LYSE™ lysozyme solution (Epicentre), and a negative control contained only resuspended cells in TEN or P1 buffer.

Lysis was assessed by eye as reduction in viscosity. READY-LYSE™ started to lyse cells by about 5 minutes and totally cleared by about 15 minutes. NSP38 in TEN buffer lysed cells by about 45 minutes but did not totally clear, while NSP38 in P1 buffer did not lyse the cells.

Example 3

Bacterial Lysis by NSP38 in Fermentation Broth versus TEN Buffer

10 µl of NSP38 UFC as described in Example 2 was added to 500 µl *Bacillus licheniformis* in fermentation broth (fermented about 100 hours in LB medium at 37° C.) or to bacterial cells that were centrifuged and resuspended in TEN buffer, and incubated at 37° C. Lysis was compared to positive controls with READY-LYSE™ both fermentation broth and TEN buffer and a negative control with fermentation broth alone.

Lysis was assessed by eye as reduction in viscosity. Cells in fermentation broth exhibited a greater degree of lysis with NSP38 than cells resuspended in TEN buffer. READY-LYSE™ lysed to a greater extent than NSP38 in both buffer conditions.

Example 4

Comparison of Activities of NSP38 and Hen Egg White Lysozyme 2, 5, or 10 µl of NSP38 UFC as described in Example 2 was added to 1 ml of *Bacillus licheniformis* in fermentation broth (fermented about 100 hours in LB medium at 37° C.) and incubated at 37° C. or 45° C. for 1 hour or 2 hours. Lysis with NSP38 was compared with lysis by hen egg white lysozyme (HEWL) at a final concentration of 200 µg/ml, incubated at 45° C.

Lysis was assessed by eye as reduction in viscosity. Equivalent doses of NSP38 compared to HEWL (2 µl NSP38/ml vs. 200 µg HEWL/ml) lysed the cells, but it took about twice as long under these conditions (2 hours for NSP38 vs. 1 hour for HEWL).

Example 5

Effect of pH on Activity of NSP38

50 µl, or 250 µl of 3M sodium acetate, pH 5.5, was added to 1 ml of *Bacillus licheniformis* in fermentation broth (fermented about 100 hours in LB medium at 37° C.) containing 2 µl NSP38 UFC as described in Example 2, and incubated at 37° C. for up to 2 hours. The pH in the final mixtures was decreased from 7.5 to 6.

Lysis was assessed by eye as reduction in viscosity. The time required for total lysis in the mixture with 150 µl sodium acetate was 15 minutes, which was 8 times faster than in fermentation broth. After 15 minutes, no lysis was observed in the sample with 50 µl sodium acetate, some lysis was observed in the sample with 150 µl sodium acetate, and total lysis was observed in the sample with 250 µl sodium acetate.

Example 6

NSP38 Dose Response

75 µl of 3M sodium acetate, pH 5.5, was added to 500 µl Bacillus licheniformis in fermentation broth (fermented about 100 hours in LB medium at 37° C.). 10, 2, or 1 µl, or 5 µl of a 1:10 dilution, of NSP38 UFC as described in Example 2 were added, and the mixtures incubated at 37° C. for 30 minutes. Bacterial lysis was then determined for each sample. Lysis was assessed by eye as reduction in viscosity.

Samples incubated with 10, 2, or 1 µl were completely lysed after 30 minutes. The sample with 5 µl of a 1:10 dilution of NSP38 was lysed but at a lower level than the other samples.

Example 7

Inhibition of Microbial Growth with NSP38

60:40 (v/v) stocks of NSP38 UFC as described in Example 2 and microbial growth media were prepared and then used to prepare ⅔ serial dilution series in 96 well microtiter plates. Based on a starting concentration of about 100 mg/ml NSP38 in the NSP38 UFC, the concentrations of NSP38 tested were about 20,000, 13,333, 8,889, 5,926, 3,951, 2,634, 1,756, 1,171, 780, and 520 ppm.

Each well was inoculated with 5 µl of an overnight culture of a microbial strain and incubated for 24 hours at 37° C. (bacteria) or 30° C. (yeast and molds). Each strain was tested in duplicate.

Inhibition of microbial growth by different NSP38 dilutions was characterized by measuring optical density at 620 nm immediately after strain addition (OD0h) and after 24 hours (OD24h). Full inhibition was registered if ΔOD=OD24h−OD0h was less than 20% of the ΔOD of the same strain without addition of NSP38. A serial dilution of the sample without strain addition was used to subtract background OD from the results.

The results are summarized in the following Table:

| Species | Extended lag phase (ppm) | MIC (ppm) |
|---|---|---|
| Bacillus cereus | 780 | No bacteriostatic effect |
| Bacillus cereus (spores) | <520 | No bacteriostatic effect |
| Bacillus weihenstephanensis | 13333 | No bacteriostatic effect |
| Candida tropicalis | 3292 | 5926 |
| Candida parapsilosis | <520 | 1463 |
| Clostridium sporogenes (strain A) | 1171 | No bacteriostatic effect |
| Clostridium sporogenes (strain B) | 1756 | No bacteriostatic effect |
| Clostridium sporogenes (strain C) | 20000 | No bacteriostatic effect |
| Clostridium sporogenes (strain C spores) | 7407 | No bacteriostatic effect |
| Debaryomyces hanseii | <520 | 20000 |
| Klyveromyces marxianus (H118) | 5926 | 8889 |
| Leuconostoc mesenteroides ss | 6420 | No bacteriostatic effect |
| Listeria innocua | 20000 | No bacteriostatic effect |
| Pseudomonas fluorescens | <520 | No bacteriostatic effect |
| Rhodotorula mucilaginosa (H116) | <520 | No bacteriostatic effect |
| Rhodoturola glutinis | 8642 | No bacteriostatic effect |
| Staphylococcus aureus | 20000 | No bacteriostatic effect |
| Zygosaccharomyces bailii | 20000 | No bacteriostatic effect |

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

---

What is claimed is:

1. A method for inhibiting bacterial growth, comprising contacting a microbial cell with an NSP38 polypeptide or variant thereof, thereby inhibiting the growth of the cell, wherein the polypeptide comprises an amino acid sequence having at least 95% sequence identity to the polypeptide set forth in SEQ ID NO:4, or a mature protein produced by cleavage of a signal sequence from said polypeptide.

2. The method of claim 1, wherein the method is conducted at acidic pH.

3. The method of claim 1, wherein the polypeptide comprises an amino acid sequence having at least 98% sequence identity to the polypeptide set forth in SEQ ID NO:4, or a mature protein produced by cleavage of a signal sequence from said polypeptide.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: synthetic primer

<400> SEQUENCE: 1
atgaagtttc tgactcccct tgcc                                            24

<210> SEQ ID NO 2
<211> LENGTH: 24
<212> TYPE: DNA
<213> ORGANISM: Artificial
<220> FEATURE:
<223> OTHER INFORMATION: synthetic primer

<400> SEQUENCE: 2
ctaacttccg cgggcaatct tctg                                            24

<210> SEQ ID NO 3
<211> LENGTH: 743
<212> TYPE: DNA
<213> ORGANISM: Trichoderma reesei
<400> SEQUENCE: 3
```

```
atgaagtttc tgactcccct tgccgtccaa ttggcagccc ttgcctctat ggccagcgca      60
accgtgccag gattcgacat ttcccactac caagccaccg ttgactttgc caaagcctat     120
gccgatggtg cacgctttgt gatcatcaag gttcataccg tcttcccaac tctcatttca     180
agatgaggtg ctaaactgct gcttaggcta ctgagggcac acctacact gaccccagct      240
tcagcgatca ctataccaag gcgaccaatg ccggcttcat ccggggtggt taccactttg     300
cccagcccgc ctcctcttcc ggtgctgccc aagccaacta ctttctcaaa cacggaggcg     360
gctggtcagc ggacggcatc acacttcctg gtatgctgga tcttgagtat gctcccagcg     420
gcgacagctg ctatggcttg agcgcgagtg ccatggtcag ctggatcaac gactttgtca     480
acacttacca cgctgctacg acccagtatc ctctcattta cacctccaca agctggtggc     540
aactctgtac tgggaacaat ggctcgtttg gtagcaaatc gcctcttgtt atcgcgcggt     600
atgctagctc tgttggggcg ctgcccaatg gctggagcgt ttatacaatc tggcagaaca     660
gtgatgcctc tccctggggt ggcgataatg atatcttcaa cggaaatctc gcacaactgc     720
agaagattgc ccgcggaagt tag                                             743
```

<210> SEQ ID NO 4
<211> LENGTH: 228
<212> TYPE: PRT
<213> ORGANISM: Trichoderma reesei

<400> SEQUENCE: 4

Met Lys Phe Leu Thr Pro Leu Ala Val Gln Leu Ala Ala Leu Ala Ser
1               5                   10                  15

Met Ala Ser Ala Thr Val Pro Gly Phe Asp Ile Ser His Tyr Gln Ala
                20                  25                  30

Thr Val Asp Phe Ala Lys Ala Tyr Ala Asp Gly Ala Arg Phe Val Ile
            35                  40                  45

Ile Lys Ala Thr Glu Gly Thr Thr Tyr Thr Asp Pro Ser Phe Ser Asp
        50                  55                  60

His Tyr Thr Lys Ala Thr Asn Ala Gly Phe Ile Arg Gly Gly Tyr His
65                  70                  75                  80

Phe Ala Gln Pro Ala Ser Ser Gly Ala Gln Ala Asn Tyr Phe
                85                  90                  95

Leu Lys His Gly Gly Trp Ser Ala Asp Gly Ile Thr Leu Pro Gly
                100                 105                 110

Met Leu Asp Leu Glu Tyr Ala Pro Ser Gly Asp Ser Cys Tyr Gly Leu
            115                 120                 125

Ser Ala Ser Ala Met Val Ser Trp Ile Asn Asp Phe Val Asn Thr Tyr
        130                 135                 140

His Ala Ala Thr Thr Gln Tyr Pro Leu Ile Tyr Thr Ser Thr Ser Trp
145                 150                 155                 160

Trp Gln Leu Cys Thr Gly Asn Asn Gly Ser Phe Gly Ser Lys Ser Pro
                165                 170                 175

Leu Val Ile Ala Arg Tyr Ala Ser Ser Val Gly Ala Leu Pro Asn Gly
            180                 185                 190

Trp Ser Val Tyr Thr Ile Trp Gln Asn Ser Asp Ala Ser Pro Trp Gly
        195                 200                 205

Gly Asp Asn Asp Ile Phe Asn Gly Asn Leu Ala Gln Leu Gln Lys Ile
    210                 215                 220

Ala Arg Gly Ser
225